United States Patent
Carreira et al.

(10) Patent No.: US 6,803,471 B2
(45) Date of Patent: Oct. 12, 2004

(54) INDOLINOSPIROPYRAN COMPOUNDS AND METHODS FOR THEIR MANUFACTURE

(75) Inventors: Erick M. Carreira, Zumikon (CH); Weili Zhao, Zurich (CH)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 440 days.

(21) Appl. No.: 10/058,994

(22) Filed: Jan. 28, 2002

(65) Prior Publication Data
US 2002/0087010 A1 Jul. 4, 2002

Related U.S. Application Data

(62) Division of application No. 09/585,108, filed on May 31, 2000, now Pat. No. 6,521,753.

(51) Int. Cl.⁷ ...................... C07D 491/107; C09K 9/02
(52) U.S. Cl. ......................................... 548/409; 544/71
(58) Field of Search ............................ 544/71; 548/409

(56) References Cited

U.S. PATENT DOCUMENTS

| | | | | | |
|---|---|---|---|---|---|
| 4,215,010 A | * | 7/1980 | Hovey et al. | ................ | 252/586 |
| 4,342,668 A | * | 8/1982 | Hovey et al. | ................ | 252/586 |
| 4,556,605 A | * | 12/1985 | Mogami et al. | ............ | 428/331 |
| 4,816,584 A | * | 3/1989 | Kwak et al. | .................... | 544/71 |
| 4,826,977 A | * | 5/1989 | Heller et al. | ................... | 544/70 |
| 4,931,221 A | * | 6/1990 | Heller | .......................... | 252/586 |
| 5,645,768 A | * | 7/1997 | Melzig et al. | ............... | 252/586 |
| 6,521,753 B1 | | 2/2003 | Carreira et al. | | |

FOREIGN PATENT DOCUMENTS

| | | | |
|---|---|---|---|
| EP | 0141407 A2 | * | 5/1985 |
| EP | 0246114 A2 | * | 11/1987 |
| EP | 0449669 A1 | * | 10/1991 |
| GB | 2174711 A | * | 11/1986 |
| WO | WO94/22850 A1 | * | 11/1994 |

OTHER PUBLICATIONS

Malaysian Search Report, dated Nov. 28, 2003, for Malaysian Appln. No. PI 2001 2551.

* cited by examiner

Primary Examiner—Bennett Celsa

(57) ABSTRACT

The present invention provides indolinospiropyran compounds and methods for their manufacture, which compounds are useful as photochromic compounds. The compounds of the invention are substituted on the indole ring with succinimide, which substitution permits ring opening of the succinimide and modulation of the bulk and photochromic properties of the compounds. The compounds may be conveniently prepared using the solid phase organic synthesis of the invention.

10 Claims, No Drawings

INDOLINOSPIROPYRAN COMPOUNDS AND METHODS FOR THEIR MANUFACTURE

This application is a divisional of U.S. application No. 09/585,108 filed May 31, 2000 now U.S. Pat. No. 6,521,753.

FIELD OF THE INVENTION

The present invention relates to spiropyran compounds. In particular, the invention provides indolinospiropyran compounds and methods for their manufacture, which compounds are useful as photochromic compounds.

BACKGROUND OF THE INVENTION

Various classes of photochromic compounds have been synthesized and suggested for use in applications in which reversible color changes or darkening is induced by sunlight. For example, spiro(indolino)naphthopyrans and spiro(indolino)quinopyrans are described in GB Patent 2,174,711. Spiropyrans also are described in Brown, Glenn H. ed., *Photochromism* (New York, 1971) and Durr, Heinz and Henri Bouas-Laurent eds., *Photochromism* (Elsevier, 1990).

Spiropyran derivatives may be the best known organic compounds showing photochromism phenomenon, but the structures of reported spiropyrans are considerably limited. Thus, a need exists both for spiropyran compounds allowing further facile modifications as well as methods for the synthesis of diverse spiropyran compounds.

DESCRIPTION OF THE INVENTION AND ITS PREFERRED EMBODIMENTS

The present invention provides indolinospiropyran compounds, and particularly photochromic indolinospiropyran compounds, as well as methods for synthesizing these compounds. The indolinospiropyran compounds of the invention are substituted on the indole ring with succinimide, which substitution permits ring opening of the succinimide and modulation of the bulk and photochromic properties of the compounds.

In one embodiment, the invention provides a compound comprising, consisting essentially of, and consisting of the formula:

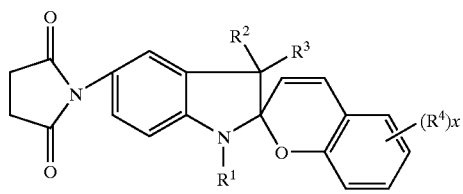

I wherein $R^1$ is $C_1$–$C_{18}$ alkyl, allyl, phenyl, mono- or disubstituted phenyl, phen($C_1$–$C_4$)alkyl, or ($C_1$–$C_4$) alkoxycarbonyl ($C_1$–$C_4$)alkyl, $R^2$ and $R^3$ are each independently $C_1$–$C_4$ alkyl, phenyl, mono- or di-substituted phenyl, benzyl, or combined to form a cyclic ring that is cyclohexyl, norbornyl or adamantyl ring, $R^4$ is hydrogen, hydroxy, trichloromethyl, trifluoromethyl, formyl, $C_1$–$C_4$ alkyl, halogen, $C_1$–$C_4$ alkoxy, nitro, cyano, $C_1$–$C_4$ monohaloalkyl, $C_1$–$C_4$ alkoxycarbonyl, or an aromatic sharing the two adjacent carbon atoms with the benzene portion of the pyran ring to form a condensed aromatic ring including, without limitation, naphthyl, phenanthrenyl, and quinolino, x equals 1, 2, or 3 provided that when x=1, $R^4$ may be located on any of the available carbon atoms of the benzene ring of the benzopyran moiety, preferably on the 6, 7, or 8 position and when x=2, each of the $R^4$ may be the same or different and located at the 6 and 8 or 5 and 7 positions, preferably at the 6 and 8 positions. $R^1$ preferably is a $C_1$–$C_4$ alkyl, phenyl, benzyl, allyl, or ethoxycarbonyl ethyl, $R^2$ and $R^3$ preferably are each independently methyl, ethyl, or phenyl and $R^4$ preferably is $C_1$–$C_4$ alkyl, $C_1$–$C_2$ alkoxy, chloro, bromo, iodo, trifluoromethyl, or nitro.

In a preferred embodiment, the invention provides a compound comprising, consisting essentially of, and consisting of the formula:

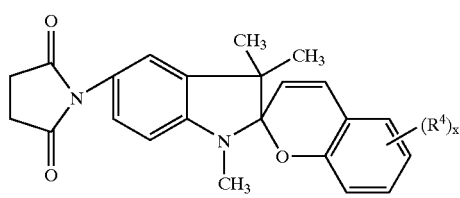

II wherein $R^4$ is hydrogen, hydroxy, trifluoromethyl, formyl, methyl, ethyl, methoxy, ethoxy, nitro, fluoro, chloro, bromo, or iodo, and x is 1 or 2.

Because the compounds of formulae I and II contain a succinimide portion, the properties of the compounds, such as solubility, sensitivity and the like, of the invention may be manipulated by ring opening of the succinimide using any of a variety of known methods. Suitable such methods are described, for example, in 48(12) *Heterocycles*, 2677–2691 (1998).

Formulae I and II compounds may be prepared by any convenient known method and preferably are prepared using a solid phase organic synthesis. The use of solid phase synthesis is advantageous in that it provides ease in execution of the reaction, ease in product purification, and convenient handling of polar molecules throughout the synthetic protocol. Additionally, this approach permits use of commercially available starting materials and use of excess reactant to drive the reaction to completion and to surpass the side reactions. Key in the synthesis is the use of a polymer-supported indoline of the formula:

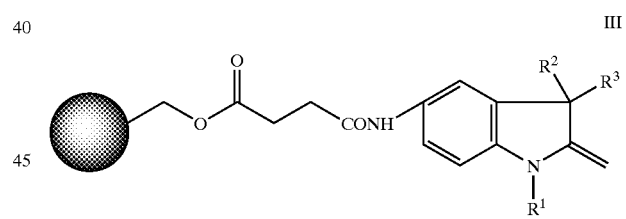

III wherein $R^1$, $R^2$, and $R^3$ are the same as for formula (I). The solid support may be selected from any of a variety of hydroxy resins. Suitable hydroxy resins include, without limitation, hydroxymethyl polystyrene resin, Wang resin (also known as 4-hydroxymethyl phenoxy resin or "HMP resin"), HMPA-PEGA resin (or 4-hydroxymethylphenoxyacetic acid and bisacrylamidoprop-1-yl polyethyleneglycol), HMPB-BHA resin (or 4-hydroxy-3-methoxyphenoxybutyric acid benzhydrylamine), HMPB-MBHA resin (4-hydroxymethyl-3-methoxyphenoxybutyric acid-methylbenzhydrylamine), and combinations thereof. The theoretical loading of the resin may be either low (e.g., less than about 0.1 mmole/g) or high (e.g., greater than about 0.4 mmole/g), but for production of greater quantities of product, preferably is high, more preferably about 0.4 to about 1.5 mmole/g. Either of about 100–200 mesh or about 200–400 mesh resin may be used. Preferred resins are an about 100–200 mesh high loading hydroxymethyl polystyrene or a Wang resin.

The solid support used will depend upon the reactants selected, the solvent used, and the product desired. The resin preferably has types and quantities of functional groups that permit efficient attachment of the reactants as well as efficient release of the product. Additionally, the resin must be swellable in the solvent used. The amount of resin used will depend on the amount of reactants used and the reaction scale desired. Generally, about 1 mg to about 100 g of resin may be used.

Formula III compounds may be prepared by either of two reaction schemes using an aminoindoline compound of the following formula:

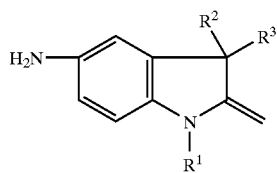

IV wherein $R^1$, $R^2$, and $R^3$ are as defined for formula I.

The reaction schemes for the preparation of the formula III compound using the aminoindolino compounds are as follows:

preferably about room temperature, under an inert atmosphere including, without limitation, argon or nitrogen, for about 3 to 24 hours. The amount of reactants used will depend on the amount of product desired and typically will be about 1 mg to about 100 g, preferably about 100 mg to about 10 g. A hydroxy resin along with diisopropyl carbodiimide ("DIC") and dimethylamino pyridine ("DMAP") then are added to the mixture to form a suspension bead. This suspension of bead is shaken under conditions suitable to carry out a coupling reaction. Suitable conditions for the reaction are a temperature of about 0 to about 60° C., preferably about room temperature, about 14 to 24 hours under an inert atmosphere. Progress of the coupling reaction may be monitored by any convenient means including, without limitation, FT-IR or single bead FT-IR. Typically, the reaction forming the indoline loaded resin is complete after 24 hours at room temperature.

In Method B, hydroxy resin is shaken with an excess of succinic anhydride under conditions suitable to carry out a coupling reaction. Suitable conditions for the reaction are a temperature of about 60 to 120° C., preferably about 70 to about 100° C., for about 10 to about 60 hours, preferably about 24 to about 48 hours. The progress of the reaction may be monitored by any convenient means and, generally, will be complete after 48 hours of refluxing. After completion of the reaction, excess succinic anhydride is washed away and the resin, now coupled with the succinic acid, is treated with

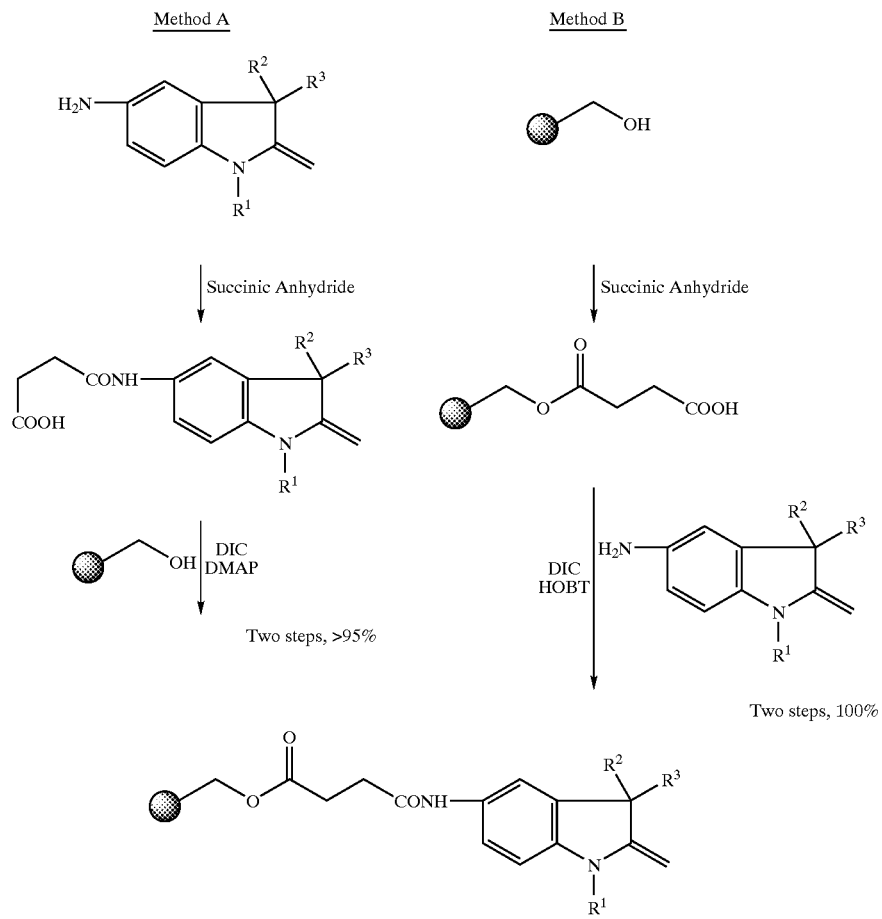

In Method A, an aminoindoline compound of formula IV is treated with succinic anhydride under conditions suitable to form succinamic acid. More specifically, the reaction is carried out at a temperature of about 0 to about 60° C., an aminoindoline of formula IV along with 1-hydroxy benzotriazole ("HOBT") and DIC. Conditions suitable for the treatment are a temperature of about 0 to 60° C., preferably room temperature, and an inert atmosphere.

In either method, loading typically is over about 95 percent. Any convenient method for testing loading may be used including, without limitation, as disclosed in 63(3) *J. Org. Chem.*, 708–718 (1998). Hexamethyldisiloxane ("HMDSO") may be used as an internal standard for purposes of ¹HNMR testing.

The aminoindoline compounds of formula IV may be prepared by reduction of nitroindoline derivatives of the formula:

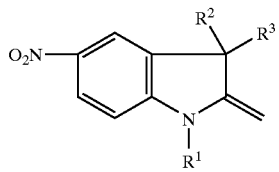

V wherein $R^1$, $R^2$, and $R^3$ are as for formula I. Suitable nitroindoline derivatives for formula V may be prepared by nitration of indoline derivatives as described in 101(8) *Bull. Soc. Chim. Bdg.*, 719–739 (1992). The indoline derivatives may be nitrated by nitric acid in cold sulfuric acid below 10° C., preferably below 7° C., over about 10 hours.

In solid phase synthesis of the indolinospiropyran compounds of the invention, a resin loaded with indoline, generally about 100 mg to about 100 g, preferably about 100 mg to about 10 g, as in formula III may be split and treated with any of a variety of salicylaldehyde derivatives under conditions suitable to form the desired indolinospiropyran compound. Suitable conditions for carrying out the synthesis are a temperature of about 50 to 120° C. under an inert atmosphere for a time of about 14 to about 11 days, preferably about 14 hours to about 3 days. Suitable salicylaldehyde derivatives are of the formula:

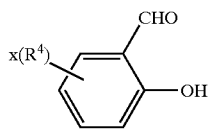

VI wherein $R^4$ and x are as for formula I.

The solid phase synthesis proceeds as follows:

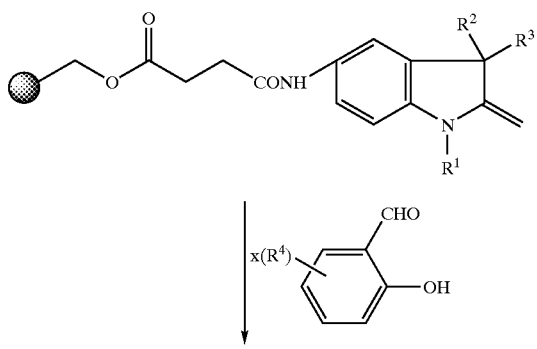

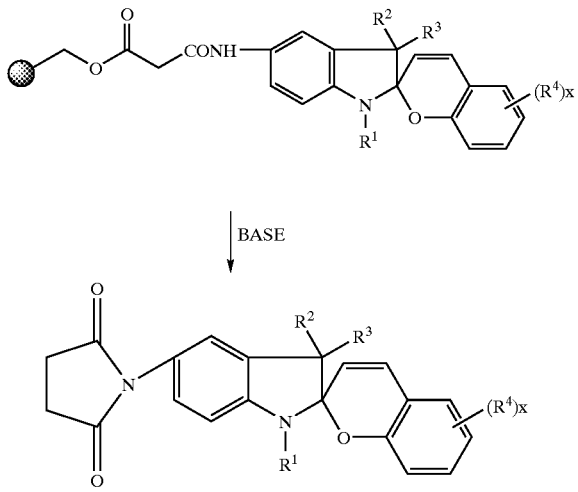

The synthesis is carried out in any suitable solvent, preferably in dioxane, dimethylformamide ("DMF"), N-methylprrolidone ("NMP"), tetrahydrofuran ("THF"), or combinations thereof. Release of the formula I compound from the solid support may be carried out in any convenient manner such as by a base-catalyzed process using any suitable base including, without limitation, piperidine, DBU, sodium methoxide, potassium tert-butyloxide. In general, about 3 to about 4 equivalents of salicylaldehyde derivative is used to react with about 1.1 to about 10 equivalents, preferably about 2 to about 5, more preferably about 3 to about 4 equivalents of resin loaded with indoline.

The compounds of the invention are useful in any of the wide variety of applications, such as ophthalmic lenses, windshields, windows, and the like in which photochromism is useful. More specifically, an effective amount of the compounds of the invention are incorporated into or coated onto an ophthalmic lens, windshield, window, or like article. The article into which the compound is incorporated or onto which it is coated will darken with exposure to ultra-violet light and revert to its original color or colorless condition in when not exposed to UV light at ambient temperatures. An effective amount of the compound is an amount of about $10^{-5}$ to about $10^{-2}$ mol/l, preferably about $10^{-5}$ to about $10^{-3}$ mol/l. Methods for incorporating into or coating such articles with photochromic compounds such as those of the invention are well know in the art.

The invention will be clarified by considering the following, non-limiting examples.

EXAMPLES

Example 1

5-Nitro-1,3,3-trimethyl-indoline 2,3,4-Trimethyl-indoline (17.3, 0.1 mole) was added to 45 ml cold sulfuric acid drop-wise at below 5° C. with stirring. 7.0 g Nitric acid (1 mole) in 18 mL sulfuric acid then were added drop-wise with stirring over 1 hr while keeping the temperature below 7° C. Stirring was continued for 3 hrs at 7° C. After allowing the mixture to stand in the refrigerator overnight, the orange-brown solution was poured onto crushed ice and neutralized carefully with aqueous sodium hydroxide to a pH of 4–5. The resultant orange-red precipitate was filtered by suction and washed thoroughly with water before being taken up with ether. The etherate solution as dried with anhydrous sodium sulphate, solvent was removed and the residue re-crystallized from methylene chloride to give 13 g of a yellow-brown solid. The yield of 5-nitro-1,3,3-trimethyl-indoline was 59.6%.

Example 2

5-Amino-1,3,3-trimethyl-indoline

5-Nitro-1,3,3-trimethyl-indoline (8.16 g, 40 mmole) was added to a solution of stannous chloride (53 g, 280 mmole) in 200 ml hydrochloric acid with stirring. The mixture was gently refluxed for 16 hrs. The cold reaction mixture was poured onto crushed ice, made alkaline with a concentrated solution of sodium hydroxide and extracted with ethyl acetate (4×200 ml). The combined ethyl acetate solutions were dried with anhydrous sodium sulphate and decolorized with a small amount of active carbon. Solvent was removed and the residue re-crystallized from ethyl acetate to 5.96 g of a yellow solid, an 80% yield of 5-amino-1,3,3-trimethyl-indoline.

Example 3a

1,3,3-Trimethyl-indoline-5-yl-succinic amide Wang ester

Under nitrogen atmosphere, 5-amino-1,3,3-trimethyl indoline (1.94 g, 10.3 mmole) in 5 ml anhydrous tetrahydrofuran was added drop-wise to 5 ml THF in solution with 1.0 g (10 mmole) succinic anhydride over 1 hr. The mixture was stirred at room temperature for 7 hrs. Wang resin (theoretical loading 1.28 mmole/g, 5 g, 6.4 mmole), diisopropyl carbodiimide (1.26 g, 10 mmole) and DMAP (61.1 mg, 0.5 mmole) were added. The suspension was shaken at room temperature for 24 hours and then filtered through glass sinter, washed with THF (4×15 ml), DMF (4×15 ml), dichloromethane (4×10 ml) and dried in vacuo. A 7.82 g bead was obtained.

50.9 mg of the bead was swelled in 1 ml THF and released with 0.01 M THF solution of potassium tert-butoxide (3×0.2 ml, 3×15 min.). The combined THF solution was shaken with finely powdered sodium dihydrophosphate and anhydrous sodium sulphate and filtered and washed with THF. Solvent was removed in vacuo. Chloroform was added to the residue and then removed in vacuo to remove trace THF. The residue was dried in vacuo and 1 ml, 0.01 M hexamethyldisiloxane in $CDCl_3$ was added. From the integral of the proton of N—Me or succinyl versus that of the internal standard, the loading of 1,3,3-trimethyl-indoline-5-yl-succinic amide Wang ester was calculated to be 95.6%.

Example 3b

Wang resin (theoretical loading 1.28 mmole/g, 3.0 g, 3.84 mmole), 2.0 g (20 mmole) succinic acid, and 47 mg (0.38 mmole) DMAP were refluxed in THF for 48 hrs, cooled down, filtered through glass sinter and washed with THF (3×10 ml), DMF (3×10 ml), dichloromethane (2×10 ml), methanol ( 3×10 ml) and dichloromethane (2×10 ml). After drying in vacuo, 3.524 g of a white resin was obtained.

A 1.37 g (1.5 mmole) suspension bead of the resin, 5-amino-1,3,3-trimethyl indoline (3.76 g, 2.0 mmole), HOBT (12% water, 322 mg, 2.1 mmole) and DIC (265 mg, 2.1 mmole) in 15 ml THF were shaken overnight at room temperature under nitrogen, filtered through glass sinter and washed with THF (3×5 ml), water (2×5 ml), DMF (2×3 ml), THF (3×3 ml) and dichloromethane (3×3 ml). After drying in vacuo, a 1.725 g purple bead of 1,3,3-trimethyl-indoline-5-yl-succinic amide Wang ester was obtained. The loading was determined to be quantitative using the method as described in Example 3a.

Example 4

5-Succinimido-1',3',3'-trimethyl-spiro-[2H-1-benzopyran-2,2'-indoline]

The bead split from Example 3a (0.243 g, corresponding to 0.2 mmole theoretical load) was swelled in 3 ml DMF under nitrogen for 1 hr, then shaken with 100 mg (0.8 mmole) salicylaldehyde at 60° C. for 14 hrs then cooled, filtered through glass sinter and washed with DMF (5×3 ml) and stayed at 3 ml DMF overnight. Filtering was again carried out as well as washing with DMF (3×3 ml), dichloromethane (3×3 ml), THF (3×2 ml) and anhydrous THF (3×2 ml).

The bead suspended in 2 ml THF was added to 0.25 ml (0.1 M) THF solution of potassium tert-butoxide, stayed for 15 to 20 minutes, filtered and washed with 1 ml anhydrous THF. The release procedure was repeated using 0.1 to 0.15 ml (0.1 M) THF solution of potassium tert-butoxide. The combined THF solution was shaken with a small amount of finely powdered sodium dihydrophosphate, filtered, solvent removed, and the residue dried in vacuo. An 80.5 mg viscous oil was obtained for a 106.6% yield of 96.4% purity 5-Succinimido-1',3',3'-trimethyl-spiro-[2H-1-benzopyran-2,2'-indoline].

Example 5

6-Bromo-5'-succinimido-1',3',3'-trimethyl-spiro-[2H-1-benzopyran-2,2'-indoline]

The procedure of Example 4 was repeated except that 5-bromo-salicylaldehyde (121 mg, 0.6 mmole) was used. The yield of 94.3% purity 6-bromo-5'-succinimido-1',3',3'-trimethyl-spiro-[2H-1-benzopyran-2,2'-indoline] was 118%.

Example 6

6–Chloro-5'-succinimido-1',3',3'-trimethyl-spiro-[2H-1-benzopyran-2,2'-indoline]

The procedure of Example 4 was repeated except that 5-chloro-salicylaldehyde (95 mg, 0.6 mmole) was used. The yield of 97.6% purity 6-chloro-5'-succinimido-1',3',3'-trimethyl-spiro-[2H-1-benzopyran-2,2'-indoline] was 111.8%.

Example 7

6-F-5'-succinimido-1',3',3'-trimethyl-spiro-[2H-1-benzopyran-2,2'-indoline]

The procedure of Example 4 was repeated except that 5-F-salicylaldehyde (84 mg, 0.6 mmole) was used. The yield of 97.6% purity 6-F-5'-succinimido-1',3',3'-trimethyl-spiro-[2H-1-benzopyran-2,2'-indoline] was 119.4%.

Example 8

6-Nitro-5'-succinimido-1',3',3'-trimethyl-spiro-[2H-1-benzopyran-2,2'-indoline]

The procedure of Example 4 was repeated except that 5-nitrosalicylaldehyde (100 mg, 0.6 mmole) was used. The yield of 97.9% purity 6-nitro-5'-succinimido-1',3',3'-trimethyl-spiro-[2H-1-benzopyran-2,2'-indoline] was 119.8%.

Example 9

6,8-Dichloro-5'-succinimido-1',3',3'-trimethyl-spiro-[2H-1-benzopyran-2,2'-indoline]

The procedure of Example 4 was repeated except that 3,5-dichlorosalicylaldehyde (115 mg, 0.6 mmole) was used. The yield of 97.8% purity 6,8-dichloro-5'-succinimido-1',3',3'-trimethyl-spiro-[2H-1-benzopyran-2,2'-indoline] was 107.7%.

Example 10

6,8-Dibromo-5'-succinimido-1',3',3'-trimethyl-spiro-[2H-1-benzopyran-2,2'-indoline]

The procedure of Example 4 was repeated except that 3,5-dibromosalicylaldehyde (167 mg, 0.6 mmole) was used. The yield of 97.6% purity 6,8-dibromo-5'-succinimido-1',3',3'-trimethyl-spiro-[2H-1-benzopyran-2,2'-indoline] was 106.6%.

Example 11
6,8-Diiodo-5'-succinimido-1',3',3'-trimethyl-spiro-[2H-1-benzopyran-2,2'-indoline]

The procedure of Example 4 was repeated except that 3,5-diiodosalicylaldehyde (225 mg, 0.6 mmole) was used. The yield of 97.7% purity 6,8-diiodoo-5'-succinimido-1',3',3'-trimethyl-spiro-[2H-1-benzopyran-2,2'-indoline] was 99.5%.

Example 12
6-Bromo-8-methoxy-5'-succinimido-1',3',3'-trimethyl-spiro-[2H-1-benzopyran-2,2'-indoline]

The procedure of Example 4 was repeated except that 5-bromo-2-hydroxy-3-methoxybenzaldehyde (139 mg, 0.6 mmole) was used. The yield of 98.6% purity 6-Bromo-8-methoxy-5'-succinimido-1',3',3'-trimethyl-spiro-[2H-1-benzopyran-2,2'-indoline] was 96.1%.

Example 13
8-Formyl-6-methyl-5'-succinimido-1',3',3'-trimethyl-spiro-[2H-1-benzopyran-2,2'-indoline]

The procedure of Example 4 was repeated except that 2-hydroxy-5-methyl-1,3-benzenedicarboaldehyde (99 mg, 0.6 mmole) was used and the suspension of bead was shaken for 24 hrs at 60° C. The yield of 96.1% purity 8-formyl-6-methyl-5'-succinimido-1',3',3'-trimethyl-spiro-[2H-1-benzopyran-2,2'-indoline] was 98.6%.

Example 14
8-Hydroxy-5'-succinimido-1',3',3'-trimethyl-spiro-[2H-1-benzopyran-2,2'-indoline]

The procedure of Example 13 was repeated except that 2,3-dihydroxybenzaldehyde (100 mg, 0.6 mmole) was used. The yield of 8-hydroxy-5'-succinimido-1',3',3'-trimethyl-spiro-[2H-1-benzopyran-2,2'-indoline] was 112.6%.

Example 15
6-Methyl-5'-succinimido-1',3',3'-trimethyl-spiro-[2H-1-benzopyran-2,2'-indoline]

The procedure of Example 4 was repeated except that 5-methyl-salicylaldehyde (82 mg, 0.6 mmole) was used and the suspension of bead was shaken at 60° C. for 24 hrs and then for 14 hrs at 80° C. The yield of 96.3% purity 6-methyl-5'-succinimido-1',3',3'-trimethyl-spiro-[2H-1-benzopyran-2,2'-indoline] was 95.9%.

Example 16
8-Methyl-5'-succinimido-1',3',3'-trimethyl-spiro-[2H-1-benzopyran-2,2'-indoline]

The procedure of Example 15 was repeated except that 3-methyl-salicaldehyde (82 mg, 0.6 mmole) was used. The yield of 96.3% purity 6-methyl-5'-succinimido-1',3',3'-trimethyl-spiro-[2H-1-benzopyran-2,2'-indoline] was 103.7%.

Example 17
6-Methoxy-5'-succinimido-1',3',3'-trimethyl-spiro-[2H-1-benzopyran-2,2'-indoline]

The procedure of Example 4 was repeated except that 2-hydroxy-5-methoxybenzaldehyde (91 mg, 0.6 mmole) was used and the suspension of bead was shaken at 60° C. for 18 hrs and then for 14 hrs at 80° C. The yield of 96.1% purity 6-methoxy-5'-succinimido-1',3',3'-trimethyl-spiro-[2H-1-benzopyran-2,2'-indoline] was 97.2%.

Example 18
8-Ethoxy-5'-succinimido-1',3',3'-trimethyl-spiro-[2H-1-benzopyran-2,2'-indoline]

The procedure of Example 17 was repeated except that 2-hydroxy-3-ethoxybenzaldehyde (99 mg, 0.6 mmole) was used. The yield of 96.4% purity 8-ethoxy-5'-succinimido-1',3',3'-trimethyl-spiro-[2H-1-benzopyran-2,2'-indoline] was 98.8%.

Example 19
8-Methoxy-5'-succinimido-1',3',3'-trimethyl-spiro-[2H-1-benzopyran-2,2'-indoline]

The procedure of Example 4 was repeated except that 0-vanillin (91 mg, 0.6 mmole) was used. The yield of 96.6% purity 8-methoxy-5'-succinimido-1',3',3'-trimethyl-spiro-[2H-1-benzopyran-2,2'-indoline] was 110%.

Example 20
6-Trifluoromethoxy-5'-succinimido-1',3',3'-trimethyl-spiro-[2H-1-benzopyran-2,2'-indoline]

The procedure of Example 4 was repeated except that 2-hydroxy-5-trifluoromethoxybenzaldehyde (95 mg, 0.46 mmole) was used and the suspension of bead was shaken at room temperature for 18 hrs and then for 3 hrs at 60° C. The yield of 6-trifluoromethoxy-5'-succinimido-1',3',3'-trimethyl-spiro-[2H-1-benzopyran-2,2'-indoline] was 88%.

Example 21
6-Hydroxy-5'-succinimido-1',3',3'-trimethyl-spiro-[2H-1-benzopyran-2,2'-indoline]

The procedure of Example 4 was repeated except that 2,5-dihydroxylbenzaldehyde (100 mg, 0.6 mmole) was used and the suspension of bead was shaken at 60° C. for 24 hrs and then for 15 hrs at 80° C. The yield of 6-hydroxy-5'-succinimido-1',3',3'-trimethyl-spiro-[2H-1-benzopyran-2,2'-indoline] was 103.2%.

Example 22
6-tert-Butyl-5'-succinimido-1',3',3'-trimethyl-spiro-[2H-1-benzopyran-2,2'-indoline]

The procedure of Example 21 was repeated except that 5-tert-butyl-salicylaldehyde (107 mg, 0.6 mmole) was used. The yield of 96.6% purity 6-tert-butyl-5'-succinimido-1',3',3'-trimethyl-spiro-[2H-1-benzopyran-2,2'-indoline] was 89.4%.

Example 23
8-tert-Butyl-5'-succinimido-1',3',3'-trimethyl-spiro-[2H-1-benzopyran-2,2'-indoline]

The procedure of Example 21 was repeated except that 3-tert-butyl-salicylaldehyde (107 mg, 0.6 mmole) was used and the suspension of bead was shaken at 60° C. for 18 hrs and then for 14 hrs at 80° C. The yield of 96% purity 8-tert-butyl-5'-succinimido-1',3',3'-trimethyl-spiro-[2H-1-benzopyran-2,2'-indoline] was 97.7%.

Example 24
6,8-Di-tert-butyl-5'-succinimido-1',3',3'-trimethyl-spiro-[2H-1-benzopyran-2,2'-indoline]

The procedure of Example 4 was repeated except that 3,5-di-tert-butyl-salicylaldehyde (180 mg, 0.6 mmole) was used and the suspension of bead was shaken at 60° C. for 18 hrs and then for 14 hrs at 80° C. The yield of 95% purity 6,8-ditert-butyl-5'-succinimido-1',3',3'-trimethyl-spiro-[2H-1-benzopyran-2,2'-indoline] was 101.2%.

Example 25
7-Methoxy-5'-succinimido-1',3',3'-trimethyl-spiro-[2H-1-benzopyran-2,2'-indoline]

The procedure of Example 4 was repeated except that 2-hydroxy-4-methoxybenzaldehyde (91 mg, 0.6 mmole) was used and the suspension of bead was shaken at 60° C. for 58 hrs and then for 14 hrs at 80° C. The yield of 7-methoxy-5'-succinimido-1',3',3'-trimethyl-spiro-[2H-1-benzopyran-2,2'-indoline] was 82.1%.

Example 26
5,7-Dimethoxy-5'-succinimido-1',3',3'-trimethyl-spiro-[2H-1-benzopyran-2,2'-indoline]

The procedure of Example 4 was repeated except that 2-hydroxy-4,6-dimethoxybenzaldehyde (240 mg, 2.0 mmole) was used and the suspension of bead was shaken at 60° C. for 24 hrs and then for 11 days at 80° C. The yield of 96.8% purity 5,7-dimethoxy-5'-succinimido-1',3',3'-trimethyl-spiro-[2H-1-benzopyran-2,2'-indoline] was 82.9%.

Example 27
8-Methoxy-6-nitro-5'-succinimido-1',3',3'-trimethyl-spiro-[2H-1-benzopyran-2,2'-indoline]

162 mg of the bead split from Example 3b and corresponding to 0.14 mmole theoretical loading was swelled in 3 ml DMF under nitrogen for 1 hr, shaken with 8-methoxy-5-nitro salicylaldehyde (83 mg, 0.42 mmole) at 60° C. for 14 hrs. The suspension was cooled, filtered through glass sinter, washed with DMF (5×1 ml), stayed at 3 ml DMF overnight, filtered again and washed with DMF (3×1 ml), THF (3×1 ml), dichloromethane (3×2 ml) and THF (3×2 ml). To the bead suspended in 1 ml THF was added 1 ml, 0.1 M THF solution of DBU, stayed for 10 hrs, filtered and washed with THF (2×1 ml). The release procedure was repeated twice. The combined THF solution was passed by a short silica column eluted with THF to remove DBU. Solvent was removed and the residue dried in vacuo for a 104.6% yield of 8-methoxy-6-nitro-5'-succinimido-1',3',3'-trimethyl-spiro-[2H-1-benzopyran-2,2'-indoline].

What is claimed is:

1. A method for producing an indolinospiroyran compound comprising the steps of:
   (i.) providing an indoline loaded resin of the formula:

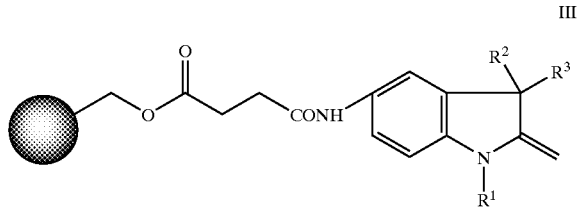

III wherein wherein $R^1$ is $C_1$–$C_{18}$ alkyl, allyl, phenyl, mono- or disubstituted phenyl, phen($C_1$–$C_4$)alkyl, or ($C_1$–$C_4$) alkoxycarbonyl ($C_1$–$C_4$)alkyl, $R^2$ and $R^3$ are each independently $C_1$–$C_4$ alkyl, phenyl, mono- or di-substituted phenyl, benzyl, or combined to form a cyclic ring that is a cyclohexyl, norbornyl or adamantyl ring;
   (ii.) treating the loaded resin, under conditions suitable to form the indolinospiropyran compound, with a salicylaldehyde derivative of the formula:

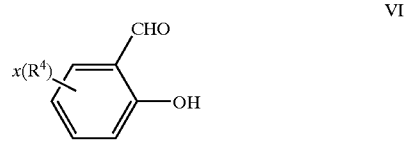

VI wherein $R^4$ is hydrogen, hydroxy, trichloromethyl, trifluoromethyl, formyl, $C_1$–$C_4$ alkyl, halogen, $C_1$–$C_4$ alkoxy, nitro, cyano, $C_1$–$C_1$ monohaloalkyl, $C_1$–$C_4$ alkoxycarbonyl, or an aromatic sharing the two adjacent carbon atoms with the benzene portion of the pyran ring to form a condensed aromatic ring, and x equals 1, 2, or 3 to produce the indolinospiropyran compound; and
   (iii.) releasing the indolinospiropyran compound.

2. The method of claim 1, wherein the resin is a hydroxy resin.

3. The method of claim 2, wherein the hydroxy resin is a hydroxymethyl polystyrene resin, a Wang resin, HMPA-PEGA resin, HMPB-BHA resin, HMPB-MBHA resin, or a combination thereof.

4. The method of claim 1, wherein the resin is of an about 100–200 mesh or an about 200–400 mesh.

5. The method of claim 2, wherein an about 100–200 mesh, high loading hydroxymethyl polystyrene resin or a Wang resin is used.

6. The method of claim 1, further comprising the step of preparing the indoline loaded resin by:
   (i.) treating an aminoindoline compound of the formula

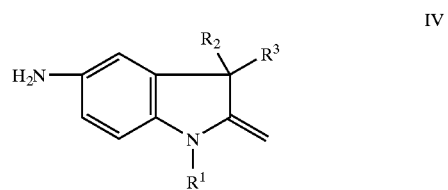

IV wherein $R^1$ is $C_1$–$C_{18}$ alkyl, allyl, phenyl, mono- or disubstituted phenyl, phen($C_1$–$C_4$)alkyl, or ($C_1$–$C_4$) alkoxycarbonyl ($C_1$–$C_4$)alkyl, $R^2$ and $R^3$ are each independently $C_1$–$C_4$ alkyl, phenyl, mono- or di-substituted phenyl, benzyl, or combined to form a cyclic ring that is a cyclohexyl, norbornyl or adamantyl ring, with succinic anhydride;
   (ii.) adding, subsequently to the mixture a hydroxy resin, diisopropyl carbodiimide and dimethylamino pyridine to form a suspension bead; and
   (iii.) shaking the suspension bead to form the indoline loaded resin.

7. The method of claim 1, further comprising preparing the indoline loaded resin by:
   (i.) shaking an excess of hydroxy resin with an excess of succinic anhydride at a temperature of about 60 to 120° C. for about 24 to 48 hours to couple the resin and succinic acid;
   (ii.) washing away, subsequently, excess succinic anhydride; and
   (iii.) treating, with 1-hydroxy benzotriazole and DIC at about 0 to 60° C. and under an inert atmosphere, the coupled resin and succinic acid with an aminoindoline of the formula IV:

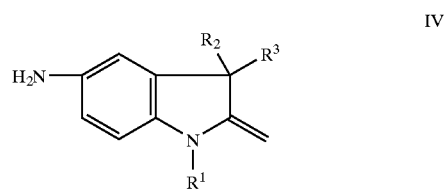

IV wherein $R^1$ is $C_1$–$C_{18}$ alkyl, allyl, phenyl, mono- or disubstituted phenyl, phen($C_1$–$C_4$)alkyl, or ($C_1$–$C_4$) alkoxycarbonyl ($C_1$–$C_4$)alkyl, $R^2$ and $R^3$ are each independently $C_1$–$C_4$ alkyl, phenyl, mono- or di-substituted phenyl, benzyl, or combined to form a cyclic ring that is a cyclohexyl, norbornyl or adamantyl ring.

8. The method of claim 6, further comprising the steps of forming the aminoindoline compound by: reducing a nitroindoline derivative of the formula:

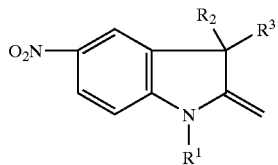

V wherein $R^1$ is $C_1-C_{18}$ alkyl, allyl, phenyl, mono- or disubstituted phenyl, phen($C_1-C_4$)alkyl, or ($C_1-C_4$) alkoxycarbonyl ($C_1-C_4$)alkyl, $R^2$ and $R^3$ are each independently $C_1-C_4$ alkyl, phenyl, mono- or di-substituted phenyl, benzyl, or combined to form a cyclic ring that is a cyclohexyl, norbornyl or adamantyl ring.

9. The method of claim 7, further comprising the steps of forming the aminoindoline compound by:

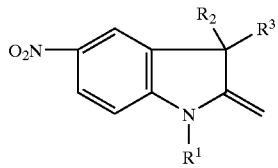

V wherein $R^1$ is $C_1-C_{18}$ alkyl, allyl, phenyl, mono- or disubstituted phenyl, phen($C_1-C_4$)alkyl, or ($C_1-C_4$) alkoxycarbonyl ($C_1-C_4$)alkyl, $R^2$ and $R^3$ are each independently $C_1-C_4$ alkyl, phenyl, mono- or di-substituted phenyl, benzyl, or combined to form a cyclic ring that is a cyclohexyl, norbornyl or adamantyl ring.

10. An indoline loaded resin of the formula:

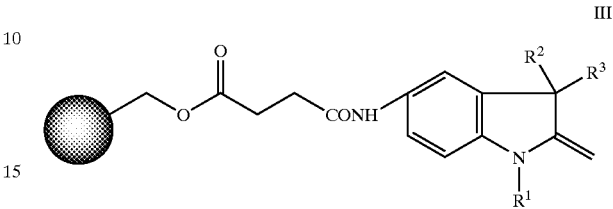

III wherein wherein $R^1$ is $C_1-C_{18}$ alkyl, allyl, phenyl, mono- or disubstituted phenyl, phen($C_1-C_4$)alkyl, or ($C_1-C_4$) alkoxycarbonyl ($C_1-C_4$)alkyl, $R^2$ and $R^3$ are each independently $C_1-C_4$ alkyl, phenyl, mono- or di-substituted phenyl, benzyl, or combined to form a cyclic ring that is a cyclohexyl, norbornyl or adamantyl ring.

* * * * *